(12) United States Patent
Hu

(10) Patent No.: US 8,298,567 B2
(45) Date of Patent: Oct. 30, 2012

(54) HYPERBRANCHED POLYUREA DELIVERY SYSTEM FOR BINDING AND RELEASE OF GROWTH FACTORS

(75) Inventor: Jin Hu, Stow, OH (US)

(73) Assignee: Michigan Molecular Institute, Midland, MI (US)

( * ) Notice: Subject to any disclaimer, the term of this patent is extended or adjusted under 35 U.S.C. 154(b) by 275 days.

(21) Appl. No.: 12/764,887

(22) Filed: Apr. 21, 2010

(65) Prior Publication Data

US 2010/0272810 A1    Oct. 28, 2010

Related U.S. Application Data

(60) Provisional application No. 61/214,324, filed on Apr. 22, 2009.

(51) Int. Cl.
*A61F 2/02* (2006.01)

(52) U.S. Cl. .................................................. 424/423

(58) Field of Classification Search .................. None
See application file for complete search history.

(56) References Cited

U.S. PATENT DOCUMENTS

| | | | |
|---|---|---|---|
| 5,476,666 A | 12/1995 | Rhee et al. | |
| 6,524,274 B1 | 2/2003 | Rosenthal et al. | |
| 6,534,600 B2 * | 3/2003 | Dvornic et al. | ......... 525/474 |
| 7,473,678 B2 | 1/2009 | Lynch | |

OTHER PUBLICATIONS

J. Tailpale and J. Keski-Oja, FASEB J., 11, 51-59 (1997).
S. Cohn et al., Pharm. Res., 8, 713 (1991).
K. Yamada et al., J. Neurosurg., 86, 871-875 (1997).
Y. Tabata and Y. Ikada, Advanced Drug Delivery Reviews, 31, 287-301 (1998).
Y. Tabata et al., Pure & Appl. Chem., 70(6), 1277-1282 (1998).
S. Chakraborty et al., Soft Matter, 2, 850-854 (2006).
E.R. Edelman, et al., Biomaterials, 12, 619-626 (1991).
E. Gu, B. Amsden and R. Neufeld, J. Controlled Release, 96(3), 463-472 (2004).
Y. J. Park et al., J. Controlled Release, 67, 385-394 (2000).

* cited by examiner

*Primary Examiner* — Carlos Azpuru
(74) *Attorney, Agent, or Firm* — Technology Law PLLC; Karen L. Kimble

(57) ABSTRACT

The present invention provides a polymer delivery system for the in vivo binding and release of growth factors, preferably orthobiologic GF, comprising a hyperbranched polymer having physiologically-acceptable anionic phosphorous groups. The hyperbranched polymer is preferred to be a polyurea with phosphonate anions. This polymer can be cross-linked to form a network and provide a coating for implanted devices.

10 Claims, 7 Drawing Sheets

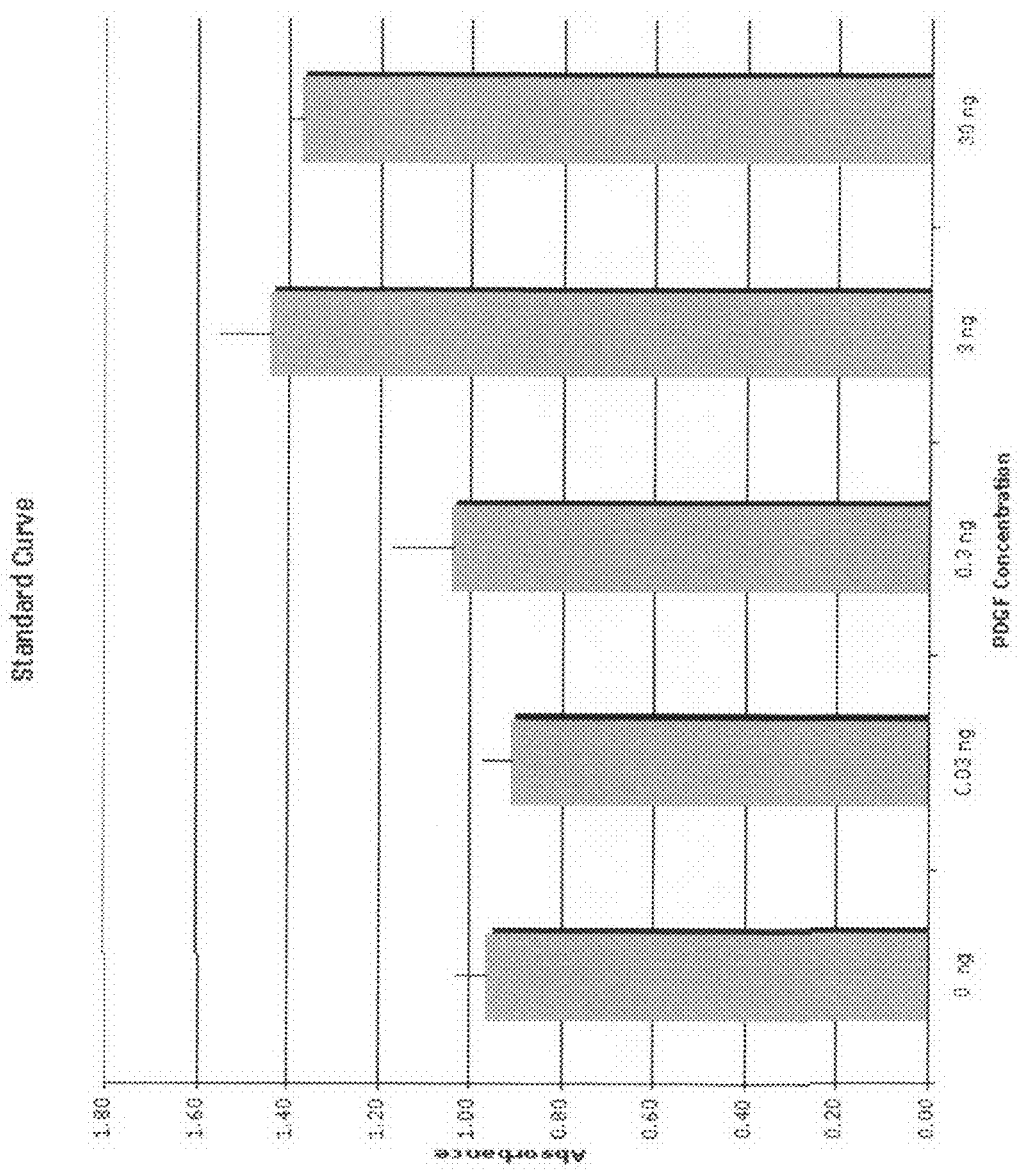

HYPERBRANCHED POLYUREA DELIVERY SYSTEM FOR BINDING AND RELEASE OF GROWTH FACTORS

CROSS REFERENCE TO RELATED APPLICATION

The present application claims benefit of priority from U.S. Provisional Application 61/214,324, filed Apr. 22, 2009.

FIELD OF THE INVENTION

The present invention provides a delivery system for growth factors to bone.

BACKGROUND OF THE INVENTION

There exist many physical conditions and diseases that cause bone loss in mammals, e.g., traumatic injures, osteoporosis, periodontal diseases, rheumatoid arthritis, and malignancies. These conditions or diseases can be treated by bone regeneration therapy. Cell growth factors are known to greatly contribute to tissue generation [for example, D. L. Stocum, *Science*, 276, 59 (1997)].

Although some treatments for bone regeneration now exist, methods of local-delivery of growth factors (GFs) for tissue regeneration have achieved only limited success because: (1) the half-life of GFs in the body is too short; (2) GFs become denatured, or lose their biological activity under some conditions, such as heating, sonication, exposure to organic solvents, or covalent bonding to carrier molecules [for example, M. S. Hora, et al. *Pharm. Res.*, 7, 1190 (1990); S. Cohen, et al., *Pharm. Res.*, 8, 713 (1991); Y. Tabata, et al. *J. Controlled Release*, 23, 55 (1993)]; and/or (3) it is difficult to achieve sustained delivery of GFs over an extended time period [for example, Y. Tabata, et al., *Biomaterials*, 19, 1781-1789 (1998); and Samuel E. Lynch, U.S. Pat. No. 7,473,678, January 2009].

Growth factors bind to the extracellular matrix (ECM), which provides a structural basis for transferring the information required for construction of complex cellular structures. The growth factors/ECM interactions involve the ionic binding of the growth factors with heparin or heparin sulfate [for example, J. Tailpale and J. Keski-Oja, *FASEB J*, 11, 51-59 (1997)]. Growth factors, such as platelet-derived growth factors (PDGF), transforming growth factors (TGFs), insulin-like growth factors (IGFs), fibroblastic growth factors (FGFs), epidermal growth factors (EGFs) and bone morphogenetic proteins (BMPs) are cationic at normal physiological pH because their amine groups are protonated under these conditions. Heparin and heparin sulfate are negatively charged because their carboxylic acid, sulfate and sulfamate functional groups are deprotonated at physiological pH. As a consequence, ionic binding takes place between the oppositely charged functional groups, and this property has been used to design GFs delivery systems for long circulation times in the body, and sustainable delivery of biologically active GFs. Examples include bio-degradable negatively charged gelatin hydrogel [for example, S. Cohen, et al., *Pharm. Res.*, 8, 713 (1991); K. Yamada, et al., *J. Neurosurg.*, 86, 871-875 (1997); Y. Tabata and Y. Ikada, *Advanced Drug Delivery Reviews*, 31, 287-301 (1998); and Y. Tabata, et al., *Pure & Appl. Chem.*, 70 (6), 1277-1282 (1998)]; poly (acrylic acid) [for example, S. Cohen, et al., *Pharm. Res.*, 8, 713 (1991); S. Chakraborty et al., *Soft Matter*, 2, 850-854 (2006)]; naturally occurring polymer material, alginate [for example, E. R. Edelman, et al., *Biomaterials*, 12, 619-626 (1991); and F. Gu, B. Amsden and R. Neufeld, *J. Controlled Release*, 96 (3), 463-472 (2004)]; chondroitin sulfate-chitosan sponge [e.g., Y. J. Park, et al., *J. Controlled Release*, 67, 385-394 (2000)]; and glycosaminoglycans [for example, W. M. Rhee and R. A. Berg, U.S. Pat. No. 5,476,666, December 1995]. These polymer materials have negatively charged carboxylate or sulfate groups. A. Rosenthal et al., U.S. Pat. No. 6,524,274, February 2003, describes the use of a hydrogel polymer to release a drug.

Thus a method to deliver various GFs sustainable for useful life at an in vivo site for bone regeneration would be of value.

BRIEF SUMMARY OF THE INVENTION

The present invention provides a delivery system for GFs to sites of device implantation in the body where bone growth is desired. More specifically, this invention provides a new polymer-based delivery system, which has multiple phosphonate anions that provide sustainable release of GFs.

This invention provides a polymer delivery system comprising a hyperbranched polymer having physiologically-acceptable anionic phosphorous groups for the in vivo binding and release of growth factors. A preferred GF is rhPDGF with a hyperbranched polymer having physiologically-acceptable anionic phosphorous groups such as phosphonate anions and phosphate anions. The hyperbranched polymer is preferred to be a polyurea with phosphonate anions. This polymer can be cross-linked to form a network and provide a coating for implanted devices.

BRIEF DESCRIPTION OF THE DRAWINGS

FIG. 5 shows in FIG. 5A a Standard Response Curve of Balb/c-3T3 to various concentrations of PDGF as seen by its release measured by absorbance.

DETAILED DESCRIPTION OF THE INVENTION

Figure 1:
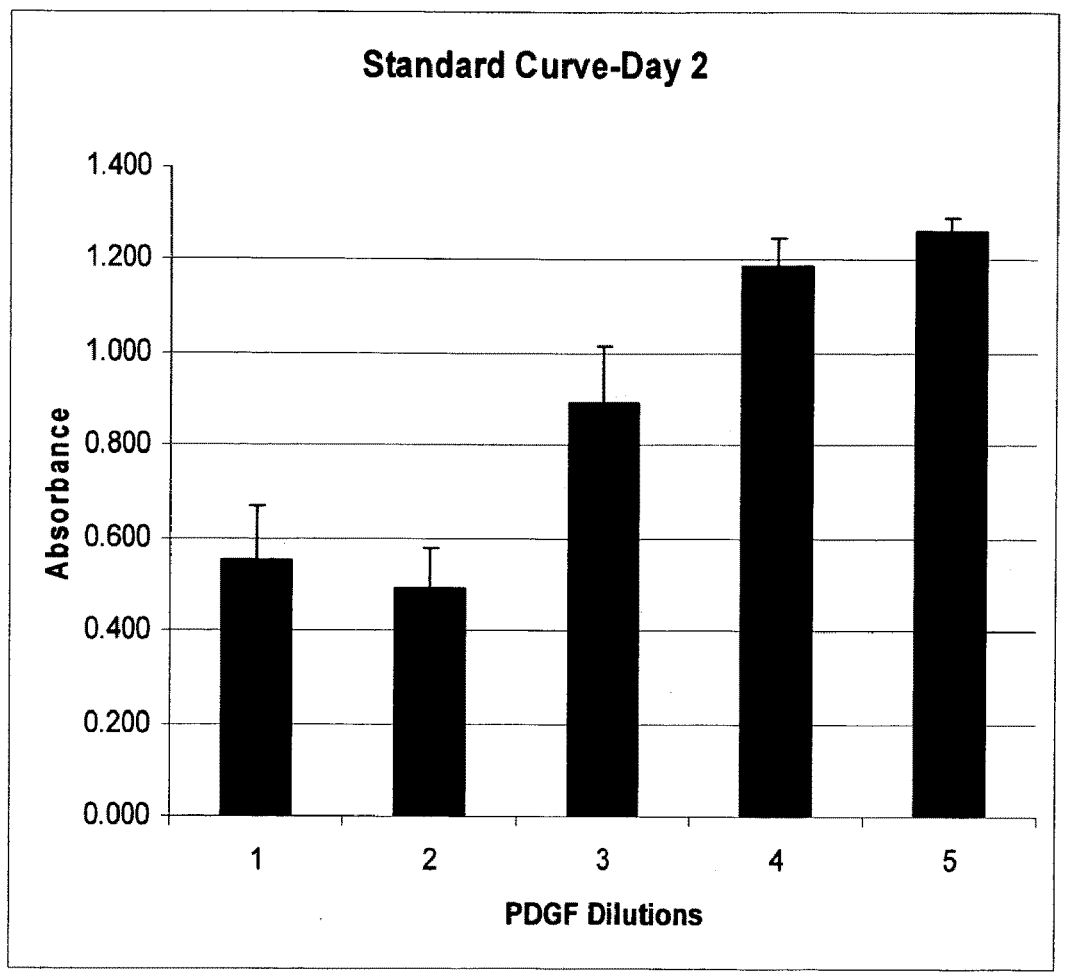
FIG. 1 shows the Standard Response Curve, after day 2, of Balb/c-3T3 to rhPDGF-BB for 5 samples, as described in Example 9.

It is understood that the terminology used herein is for the purpose of describing particular embodiments only and is not intended to be limiting. As used in this specification, the singular forms "a", "an", and "the" include plural referents unless the content clearly indicates otherwise.

Also, certain US patents have been incorporated by reference. However, the text of such patents is only incorporated by reference to the extent that no conflict exists between such text and other statements and drawings set forth herein. In the event of such conflict, then any such conflicting text in such incorporated by reference US patent is specifically not so incorporated in this patent.

GLOSSARY

The following terms as used in this application are to be defined as stated below and for these terms, the singular includes the plural.

AIBN means 2,2'-azobisisobutyrontrile
BMP(s) means bone morphogenetic proteins
DI water means deionized water
ECM means extracellular matrix
EGF(s) means epidermal growth factors
FGF(s) means fibroblastic growth factor(s)
GF(s) means growth factor(s)
HBP means hyperbranched polymer; this is a specific class of dendritic polymer and excludes dendrimers, dendrons, and dendrigrafts
hr(s). means hour(s)
IGF(s) means insulin-like growth factor(s)
min(s). means minute(s)
MWCO means molecular weight cut off
NaAc means sodium acetate
PDGF(s) means platelet-derived growth factor(s)
rhPDGF-BB means recombinant human platelet-derived growth factor
RT means ambient temperature or room temperature, from about 22 to about 25° C.
β-TCP means beta-tricalcium phosphate (commercial from BioMimetic Therapeutics, Inc. (BMTI)
TEGDA means tetra (ethylene glycol) diacrylate
TGF means transforming growth factors
XTT means an assay that quantitatively measures the amount of viable cells present through the formation and colorimetric detection of a soluble tetrazolium salt Total joint replacement is an effective treatment for relieving pain and restoring function for patients with damaged joints. This treatment involves the replacement of damaged or troubled joints with orthopedic implants and prostheses. Orthopedic implants are generally constructed of metals such as stainless steel, cobalt-chromium alloy (Co—Cr alloy), titanium alloy (Ti alloy), pure titanium (Ti) or tantalum (Ta), as well as plastics such as polyethylene. Some variants are cemented into place, while others are pressed to fit, and bone is allowed to grow into the implant for strength. Approximately 500,000 total hip and knee replacements are performed each year in the United States [National Institutes of Health Fact Sheet of Osteoarthritis at web site http://www.nih.gov/about/researchresultsforthepublic/Osteoarthritis.pdf]. These numbers will increase as the population continues to age and as the indications for joint arthroplasty extend to younger patients. For the majority of patients initial results following surgery are excellent. However, some of the prostheses may have to be revised within 5-15 years of the initial surgery because of the disappearance of bone around the implant, i.e. prosthesis-induced osteolysis ["Osteolysis and particle disease in hip replacement", A review, William H Harris, *Acta Orthor, Scand.* 65 (1): 113-123 (1994); "Osteolysis of the distal femur after total knee arthroplasty", Cadambi A, et al., *J. Arthroplasty*, 9 (6), 5, (December 1994)], which remains a major problem facing the long-term success and survival of artificial joints. Surgery to replace failures is more difficult to perform, is costly, and has a poorer outcome than the original joint replacement surgery.

One way to make bone grow into the implant and thereby improve osseointegration is to deliver bone growth factors at the implant site. Growth factors are polypeptides which bind to receptors on the cell surface, with the primary result of activating cellular proliferation and/or differentiation. Such tissue growth promoting factors have been shown to promote bone formation both in vitro and in vivo. Various groups have contributed to this field, for example, S. Cohen, et al., *Pharm. Res.*, 8, 713, (1991); Y. Tabata, et al., *J. Controlled Release* 23, 55 (1993); Y. Tabata, et al., *Biomaterials*, 19, 1781-1789 (1998); J. Tailpale, and J. Keski-Oja, *FASEB J*, 11, 51-59 (1997); K. Yamada, et al., *J. Neurosurg* 86, 871-875(1997); Y. Tabata and Y. Ikada, *Advanced Drug Delivery Reviews*, 31, 287-301 (1998); Y. Tabata, et al., *Pure & Appl. Chem.* 70 (6), 1277-1282 (1998); E. R. Edelman, et al., *Biomaterials*, 12, 619-626, (1991); F. Gu, B. Amsden and R. Neufeld, *J. Controlled Release*, 96 (3), 463-472 (2004); Y. J. Park, et al., *J. Controlled Release*, 67, 385-394, (2000); and W. M. Rhee, R. A. Berg, U.S. Pat. No. 5,476,666, December 1995. For example, combinations of PDGF and IGF-I, and PDGF and IGF-II have been shown to promote bone formation or regeneration [for example, S. E. Lynch et al., *J. Periodotol.* 62, 458-467, (1991); and U.S. Pat. No. 5,019,559].

The present invention provides a polymer delivery system comprising a hyperbranched polymer having physiologically-acceptable anionic phosphorous groups for the in vivo binding and release of growth factors. This delivery system preferably uses GF, and comprises a polymer, preferably a hyperbranched polyurea (HBP), having physiologically-acceptable anionic phosphorous groups. These phosphorous groups are phosphonate or phosphate anions.

The delivery system permits the growth factors to be released in a sustainable manner without an appreciable burst effect. In contrast prior art systems tend to release GFs too rapidly. The HBP may be cross-linked by adding a separate cross-linking agent, or alternatively, self cross-linked into a network. An injectable solution or suspension, or a hydrogel can be formed. Especially preferred are hydrogel coatings, such as TEGDA-phosphonate-polyurea HBP crosslinked via coupling with the acrylate functional groups of TEGDA, which have been previously attached to the HBP at one end. The HBP coating can bind to titanium, metal or plastic devices, and the HBP coating retains and then releases the growth factors in vivo over an extended period of time. The HBP coating may be applied when the device is manufactured, or alternatively, applied to the device just prior to implantation or injected at the site and the device implanted.

The present invention uses polymeric systems such as hyperbranched polyurea with multiple amine end-groups that are amenable to synthetic manipulation. These amine groups can be fully converted into phosphonate anions or partially converted into phosphonate anions, with the remaining amines being converted to cross-linking groups such as acrylates. The polymer with fully converted phosphonate anions can be cross-linked by divalent metal ions such as $Ca^{2+}$ or $Zn^{2+}$, or by polyalanine or dendrimer, which would consume some of the phosphonate anions to form hydrogel particles or coatings. The polymer with partially converted phosphonate anions and acrylate crosslink groups can form excellent crosslinked films or coatings on titanium surfaces.

This present polymeric system containing multiple phosphonate anions has the following advantages: (1) provides multiple, non-covalent ion-interactions with growth factors for a higher payload and better efficacy, (2) provides for release over an extended period of time, since it is unlikely that all the ionic interactions would dissociate simultaneously, (3) the phosphonate anions also act as adhesion promoters to the metal implant through co-ordination bonding, and (5) the highly phosphonated surfaces are expected to have a high affinity to calcium, and hence, also to the growing bone cells. Thus the HBP polymers of this invention form costing on such devices where the coating retains and then release the GFs in vitro as biologically active agents while retaining the polymer. Sustained release of GFs, such as orthobiologic GF, from the surface of implants coated with these polymers would enable better osseointegration, significantly extending their useful lifespan.

In vitro studies have demonstrated that this system binds PDGF growth factors and releases them over an extended period of time. Both PDGFs that are bound to the polymer carrier and those that are released showed biological activity.

The invention will be further clarified by a consideration of the following examples, which are intended to be purely exemplary of the present invention.

EXAMPLES

Example 1

Synthesis of Phosphonated Polyurea HBP Using Mannich Type Reaction

Polyurea HBP was prepared from the reaction of tris (2-aminoethyl)amine with isophorone diisocyanate at a 2:1 molar ratio using a procedure adapted from the method described in U.S. Pat. No. 6,534,600, which is incorporated by reference. The theoretical amount of amine in the polyurea HBP was 7.77 mmol/g, which is consistent with an experimental value 5.55 mmol amine/g determined by potentiometric titration determination. One g of polyurea HBP was dissolved in 10 mL of DI water. Concentrated HCl (10 mL) was added followed by phosphorous acid (1.64 g, 20 mmol) and the reaction mixture was heated to 100° C. Formaldehyde solution (3.25 mL of 37% w/w solution in DI water, 40 mmol) was added dropwise over a period of 30 min. After 4 hrs., an aliquot was removed, made basic with 50% NaOH, and a qualitative Ninhydrin test was performed. No blue color was observed. The reaction was stopped and the reaction mixture was cooled to RT. The pH was adjusted to 8 using 50% NaOH solution and then the reaction mixture was transferred to an ultrafiltration cell fitted with a 1000 MWCO regenerated cellulose membrane. Filtration was performed using DI water (3×300 mL). The retentate was concentrated and lyophilized to yield 1.5 g of fluffy pale yellow solid. The pH of the product is 8.5.

Example 2

Calcium Cross-Linked Phosphonated Polyurea HBP Powder

To a solution of the phosphonated polyurea-HBP sodium salt prepared from Example 1 in DI water (conc.: 10 mg/mL), 0.1M calcium chloride solution was added dropwise. After the addition of 0.27 mL of the calcium chloride solution, cloudiness was observed. The addition of calcium chloride solution was continued until the precipitation was complete (a total of 0.4 mL $CaCl_2$ sol). The precipitate was immediately filtered and washed with DI water and dried. The product was designated as Ca-phosphonated Polyurea HBP. It is expected that some Na-phosphonate functionalities remain in the HBP without being replaced by $Ca^{2+}$ as crosslinking by $Ca^{2+}$ does not require consuming all phosphonate groups and the precipitates were filtered immediately.

Example 3

Phosphonation of 25% of An Amine of Polyurea HBP By Mannich Type Reaction

Polyurea HBP from Example 1 (1 g, 7.77 mmol of amines) was dissolved in 10 mL of DI water. Concentrated HCl (10 mL) was added followed by phosphorous acid (0.32 g, 3.89 mmol) and the reaction mixture was heated to 100° C. Formaldehyde solution (3.25 mL, 37% wt solution in water) was added dropwise over a period of 30 mins. It was cooled to RT after being reacted for 4 hrs. The pH was adjusted to 8 using 50% NaOH solution and then the reaction mixture was transferred to an ultrafiltration cell fitted with a 1000 MWCO regenerated cellulose membrane. Filtration was performed using DI water (6×300 mL). The retentate was concentrated and lyophilized to yield 0.70 g solid, which is designated as phosphonate(25%)-polyurea HBP. Its spectral and other data are as follows:

IR on KBr disc (selected peaks in $cm^{-1}$): 3311 (—N—H), 2950 (—CH2), 1642 (C=O), 1559 (—CNH), 1508, 1468, 1382, 1365, 1305, 1250, 1037, 972, 908, 807, 748, 566;

$^{31}P$ NMR ($D_2O$, selected peaks in ppm): −17.87 (triphenyl phosphate external standard), 5.68, 5.76, 6.15, 6.21; and Phosphorous elemental analysis: 6.68%.

Example 4

Michael Addition of TEGDA To Phosphonate(25%)-Polyurea HBP

The product of Example 3, 0.2 g of phosphonate(25%)-polyurea HBP, was dissolved in 5 mL of methanol and 4 mL of TEGDA was added. The mixture was stirred vigorously at RT for 3 days. The reaction mixture was then transferred to an ultrafiltration cell fitted with a 1000 MWCO membrane and purified with 3×300 mL of methanol. The retentate was concentrated and lyophilized to yield 0.21 g of solid, which is designated as TEGDA-phosphonate (25%)-polyurea HBP. Its spectral and other data are as follows:

IR on KBr disc (selected peaks in $cm^{-1}$): 3305, 2950 (—CH2), 1734, 1648 (C=O), 1554 (—CNH), 1505, 1467, 1303, 1245, 1193, 1141, 1067, 981, 911, 807, 557;

$^1H$ NMR ($CDCl_3$, selected peaks in ppm): 0.95 (—$CH_3$), 0.97 (—$CH_3$), 1.1 (broad), 1.2 to 1.6 (multiple, weak), 2.52 to 3.12 (multiple), 3.35 (duplicable), 3.64 (multiple), 4.93, 5.90 to 6.52 (multiple, —CH=$CH_2$);

$^{31}P$ NMR ($CD_3OD$, peaks in ppm): −18.54 (triphenyl phosphate external standard), 7.19; and Phosphorous elemental analysis: 5.1%.

Example 5

Phosphonation of 50% of the Amine of Polyurea HBP By Mannich Type Reaction

Polyurea HBP from Example 1 (1 g, 7.77 mmol of amines) was dissolved in 10 mL of DI water. Concentrated HCl (10 mL) was added, followed by phosphorous acid (0.64 g, 7.78 mmol) and the reaction mixture was heated to 100° C. Formaldehyde solution (3.25 mL, 37% wt solution in water) was added dropwise over a period of 30 mins. It was cooled to RT after being reacted for 4 hrs. The pH was adjusted to 8 using 50% NaOH solution and then the reaction mixture was transferred to an ultrafiltration cell fitted with a 1000 MWCO regenerated cellulose membrane. Filtration was performed using DI water (6×300 mL). The retentate was concentrated and lyophilized to yield 0.72 g solid, which is designated as phosphonate(50%)-polyurea HBP with phosphorus elemental analysis was 8.9%.

Example 6

Michael Addition of TEGDA To Phosphonate(50%)-Polyurea HBP*

The product from Example 5, 0.2 g of phosphonate(50%)-polyurea HBP, was dissolved in 5 mL of methanol and 4 mL of TEGDA was added. The mixture was stirred vigorously at RT for 3 days. The reaction mixture was then transferred to an ultrafiltration cell fitted with a 1000 MWCO membrane and purified with 3×300 mL of methanol. The retentate was concentrated and lyophilized to yield 0.17 g, which is designated as TEGDA-phosphonate(50%)-polyurea HBP.

Example 7

Phosphonation of 75% of the Amine of Polyurea HBP By Mannich Type Reaction

Polyurea HBP from Example 1 (1 g, 7.77 mmol of amine) was dissolved in 10 mL of DI water. Concentrated HCl (10 mL) was added followed by phosphorous acid (0.96 g, 11.67 mmol) and the reaction mixture was heated to 100° C. Formaldehyde solution (3.25 mL, 37% wt solution in water) was added dropwise over a period of 30 mins. It was cooled to RT after being reacted for 4 hrs. The pH was adjusted to 8 using 50% NaOH solution and then the reaction mixture was transferred to an ultrafiltration cell fitted with a 1000 MWCO regenerated cellulose membrane. Filtration was performed using DI water (3×300 mL). The retentate was concentrated and lyophilized to yield 1.04 g, which is designated as phosphonate(75%)-polyurea HBP with phosphorus elemental analysis was 9.76%.

Example 8

Preparation of Coating Samples For rhPDGF-BB Binding And Release Tests

Part A. Coatings From Cured TEGDA-Phosphonate(50%)-Polyurea HBP

The product from Example 6, 0.01 g of TEGDA-phosphonate(50%)-polyurea HBP, was added into a small vial, followed by addition of 0.18 g methanol, 2 µL 0.1% AIBN methanol solution and 0.01 g of 10% TEGDA methanol solution. It was stirred to mix the solution until a homogenous solution was obtained. The 4 mm diameter commercially pure titanium metal (CpTi) discs were pre-treated with flame. Then a drop of the above solution was cast on the surface of the disc by a #2.5 Meyer rod. The discs were placed in an oven at 120° C. for 3 days.

Part B. Coatings From A Formulation of Phosphonate(75%)-Polyurea HBP And $CaCl_2$ The product from Example 7, 0.05 g of phosphonate (75%)-polyurea HBP, was dissolved in 2 g of DI water followed by addition of 0.9 mL of 0.1 mol/L $CaCl_2$ solution. The reaction mixture was stirred and formed a white gel-like solution. To the solution was added 0.01 g of 0.1% of AIBN methanol solution and 0.015 g of TEGDA. CpTi discs (4 mm diameter) were pre-treated with flame. Then a drop of the above solution was cast on the discs by a #2.5 Meyer rod and cured at 120° C. in an oven for 3 days.

Part C. Coatings From Cured TEGDA-Phosphonate(25%)-Polyurea HBP

The product from Example 4, 0.01 g of TEGDA-phosphonate(25%)-polyurea, in 0.18 g of methanol was added to a small vial, followed by 2 µL 0.1% AIBN methanol solution and 0.01 g of 10% TEGDA methanol solution. It was stirred and well mixed. The CpTi discs in 4 mm diameter were pre-treated with flame. Then a drop of the solution was cast on the CpTi by a #2.5 Meyer rod. The coatings on discs were cured at 120° C. in an oven for 3 days.

Additional samples were prepared by the same manner except the casting was repeated three times to form thicker coatings.

Example 9

Binding of Ca-Phosphonated Polyurea HBP With rhPDGF-BB

Part A. The Standard Response Curve of Balb/c-3T3 to rhPDGF-BB

In order to test the sensitivity of the cell line (Balb/c-3T3, ATCC#CCL 163) to the recombinant human platelet-derived growth factor (rhPDGF-BB), the response of the cells to different concentration of rhPDGF-BB was measured. The rhPDGF-BB was diluted to 30, 3, 0.3, 0.03, and 0 µg/mL (Samples no. 5, 4, 3, 2, and 1, respectively) using 20 mM of NaAc. 10 µL of the rhPDGF-BB was added in quadruplicate into the plate. Then 200 µL of NIH-3T3 cells were added into each well (5×10^4/mL). On Day 2 of the cell culture, 50 µL of XTT solution in water were added into the well to develop color for 4 hrs. The absorbance was measured by a plate reader. Under the testing condition, detecting limit for rhPDGF-BB in the cell proliferation assay as shown in FIG. 1 is approximately 15 ng/mL.

Figure 2:
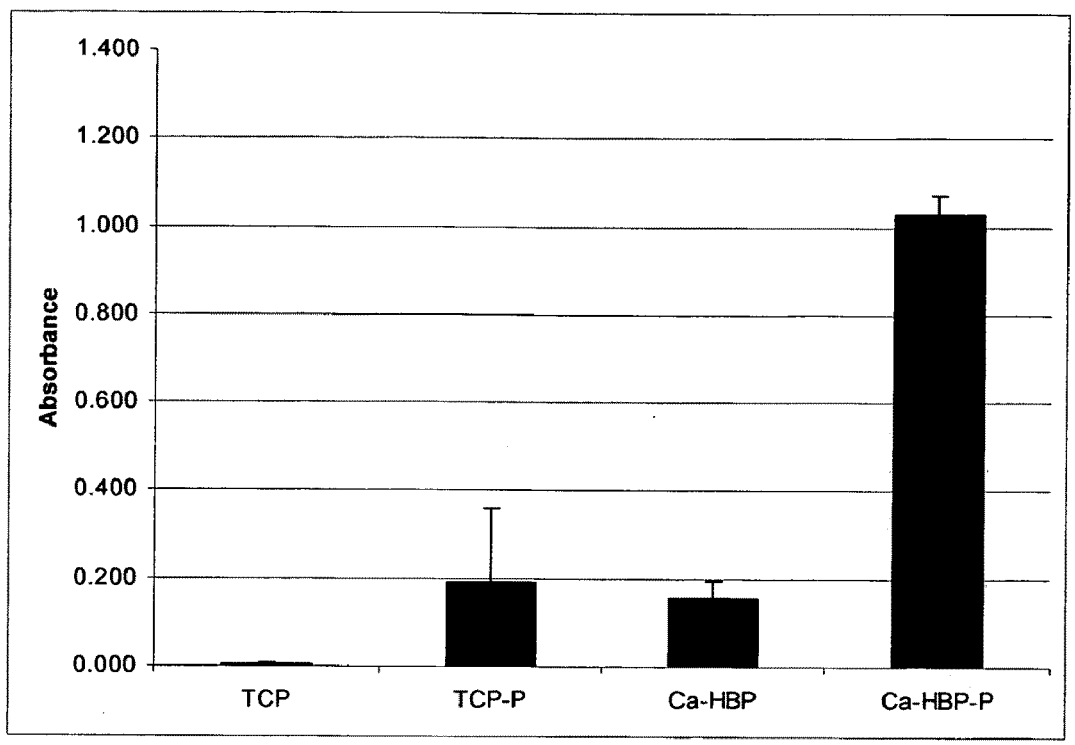
FIG. 2 shows the binding test of Ca-phosphonated polyurea HBP with rhPDGF-BB compared to tricalicum phosphate, as described in Example 9.

Part B. Test On Ca-Phosphonated Polyurea HBP Binding With rhPDGF Using Balb/c-3T3 Cell Line To test if rhPDGF-BB binds to the Ca-phosphonate HBP, 50 mg of the Ca-phosphonated polyurea HBP powder were added with 300 µL of rhPDGF (300 µg/mL). 50 mg of the control β-TCP powder was added with 200 µL of the rhPDGF-BB (300 µg/mL). The absorption was carried at 4° C. overnight. After that absorption interval the powders were washed three times with 1 mL of water and then ground into fine particles for better suspension. 10 µL of the suspension were dispensed into the wells for the measurement in quadruplicate. During the dispensing, the suspensions were shaken vigorously to have a better suspension. XTT based cell proliferation assay was carried out (Sigma-Aldrich #TOX2). It is found that all the powders alone do not stimulate cell proliferation (TCP and Ca-HBP in FIG. 2). The rhPDGF-BB absorbed by β-TCP is below the detection sensitivity (TCP-P in FIG. 1). 1 mg Ca-phosphonated polyurea HBP powder can absorb about 30 ng of rhPDGF-BB (Ca-HBP-P in FIG. 2). Cell proliferation assay was carried together with Example 9 Part A) as shown in FIG. 1. In FIG. 2 the following terms are defined:

- TCP: 10 µL from 1 mL suspension of 50 mg β-tricalcium phosphate powder in DI water.
- TCP-P: 10 µL from 1 mL suspension of 50 mg β-Tricalcium phosphate treated with 200 µL of the rhPDGF-BB (300 µg/mL) in DI water.
- Ca-HBP: 10 µL from 1 mL suspension of 50 mg of the Ca-phosphonated polyurea HBP in DI water.
- Ca-HBP-P: 10 µL from 1 mL suspension of 50 mg of the Ca-phosphonated polyurea HBP treated with 300 mL of rhPDGF-BB (300 µg/mL) in DI water.

Example 10

Release Study of rhPDGF-BB From Ca-Phosphonated Polyurea HBP

Figure 3A:
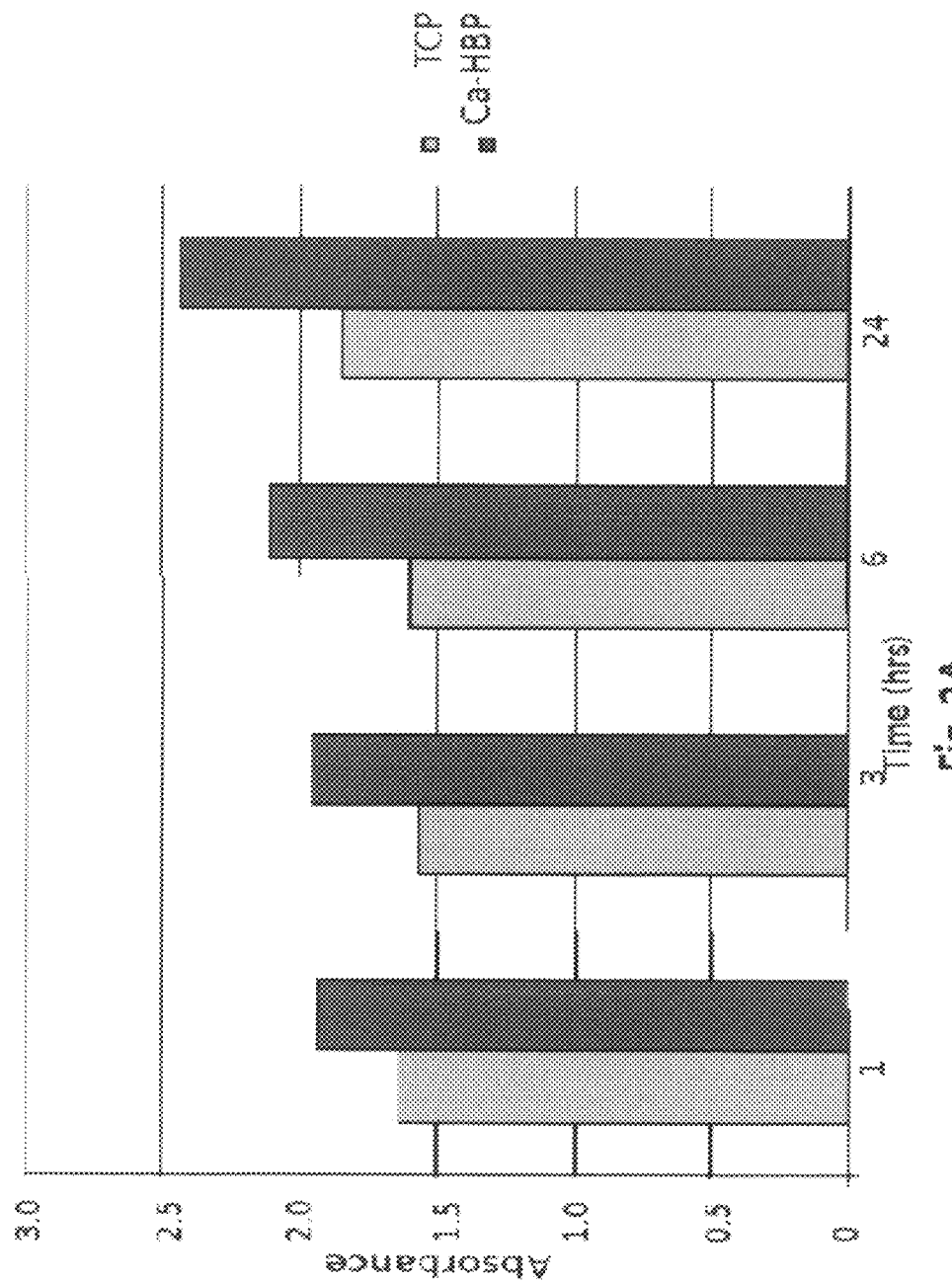
FIG. 3 shows in FIG. 3A the rhPDGF-BB release profile of Ca-Phosphonate-HBP in 20 mM of NaAc.
FIG. 3B the rhPDGF-BB release profile of Ca-Phosphonate-HBP in DI water, as described in Example 10.
Figure 3B:
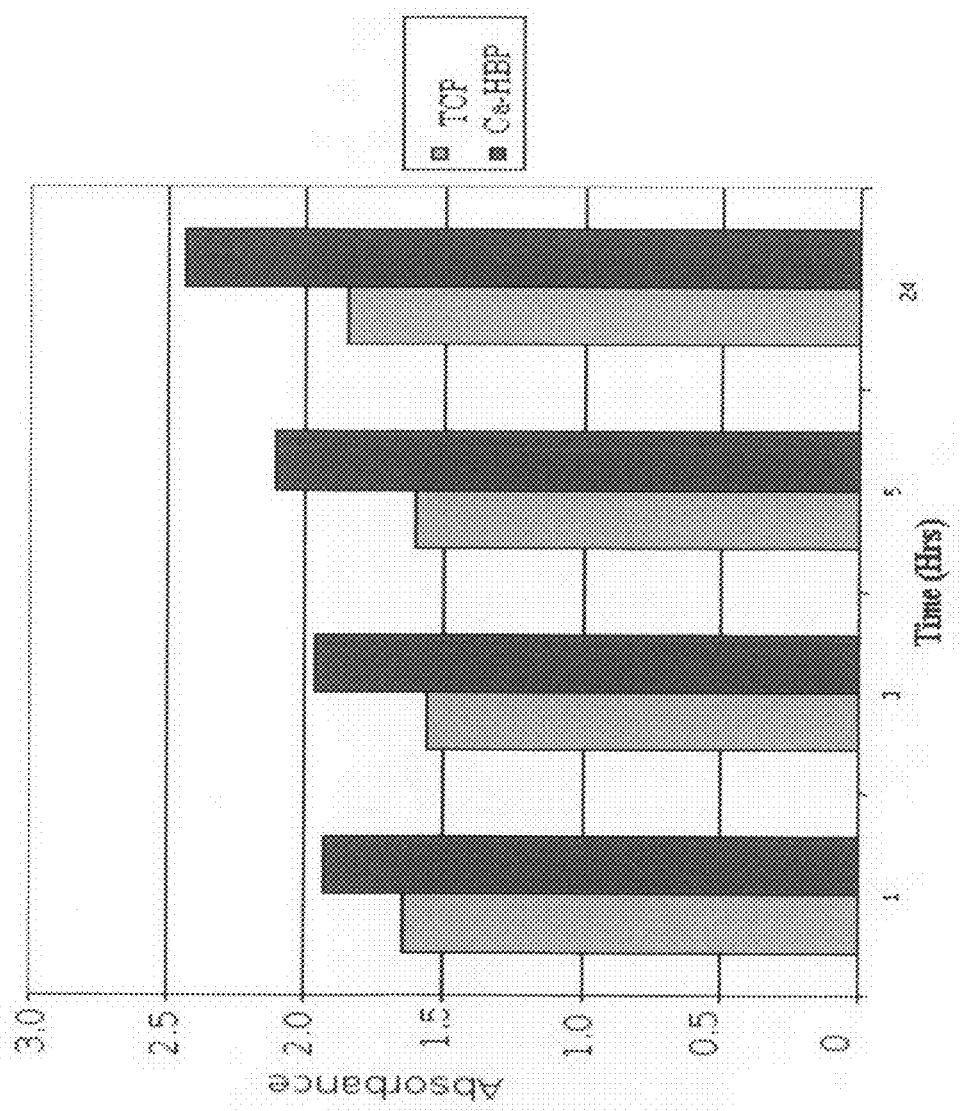

To test if the absorbed rhPDGF-BB by Ca-phosphonated polyurea HBP can be released into the solution again, 50 mg of tricalcium phosphate powder and Ca-phosphonated polyurea HBP power were incubated with 300 μL of 30 μg/mL rhPDGF-BB overnight at 4° C. (Three samples for each.) The precipitates were then washed three times with 1 mL of 20 mM of NaAc. Each time the precipitate was collected by centrifugation. 1 mL of 20 mM of NaAc was then added to incubate at RT. The release of rhPDGF-BB was tested at 1, 3, 5 and 24 hrs. At each hour point, the supernatant was collected and new buffer was added. 10 μL of the supernatant at each time point was added into the wells of the plate. The proliferation assay was then carried out similarly as in FIG. 3. Within 3 hrs, all the rhPDGF-BB associated with β-tricalcium phosphate powder was released. In contrast, rhPDGF-BB was continually released in Ca-phosphonated polyurea HBP power for at least 24 hrs. The HBP powder also absorbs much more rhPDGF as demonstrated in this experiment (FIG. 3A). Additionally, if DI water was used to wash the powders, the release of rhPDGF-BB is slower but still significant (FIG. 3B).

Example 11 rhPDGF-BB Binding On HBP Coatings On Titanium From Example 8

Figure 4:
FIG. 4 shows rhPDGF-BB binding to hyperbranched polymer coatings on titanium discs, as described in Example 11.

Titanium discs with different kinds of phosphonated HBP coatings or without coating were incubated with 100 μL of PDGF (300 μg/mL) for 48 hrs. The discs were then washed three times in sterile water and placed in a 96 well plate. Cell proliferation was carried out similarly as Examples 9 and 10. After the development of color, the supernatant was transferred to another well for measurement by the plate reader. Three types of phosphonated HBP coatings were tested as shown in FIG. 4. Coating sample of 695-62 (1-4) in FIG. 4 are thin hydrogel coatings of TEGDA-phosphonate(25%)-polyurea HBP that are crosslinked via coupling of acrylate of TEGDA. These types of coatings show almost twice the high loading of rhPDGF-BB than flame-treated Cp-Ti disc. Sample 695-62 (13-16) in FIG. 4 are thicker coatings, which could be swollen to a great degree in the aqueous medium and resulted in the delamination of the coatings. Samples 695-60-Ca in FIG. 4 are TEGDA-phosphonate(25%)-polyurea HBP that were crosslinked by both $Ca^{2+}$ and free TEGDA. For the phosphonated HBP coatings, $Ca^{2+}$ crosslinking appeared to compromise the coatings' integrity. Samples 695-59 in FIG. 4 are TEGDA-phosphonate(50%)-polyurea HBP that have too high a content of phosphonate anions, which also affect the integrity of the coatings. These phosphonated HBP coatings with poor coating integrity do not have high rhPDGF-BB loadings, but do bind rhBDGF-BB. For all the phosphonated HBP coatings, the rhPDGF-BB remains biologically active after being bound to the coatings.

Example 12 rhPDGF-BB Binding On HBP Coatings On Titanium And Comparison To Standard Response Curve Part A. The Standard Response Curve of Balb/c-3T3 To rhPDGF-BB A new standard curve comparing the response of the cell line (Balb/c-3T3, ATCC #CCL 163) to different concentrations of rhPDGF-BB in solution was generated for the purpose of side-by-side comparison with the degree of cell growth on top of titanium discs coated with phosphonated HBP, which slowly released adsorbed rhPDGF-BB. A procedure similar to Example 9 was used, in which rhPDGF-BB was diluted to 30, 3, 0.3 and 0.03 μg/mL in 20 mM of NaAc. The absorbance was measured by a plate reader. Under the conditions used, the limit of detection for rhPDGF-BB in the cell proliferation assay shown in FIG. 5A was approximately 0.3 μg/mL (final concentration at 15 ng/mL after the assay dilution).

Part B. Release of rhPDGF-BB From HBP Coatings On Titanium

Figure 5B:
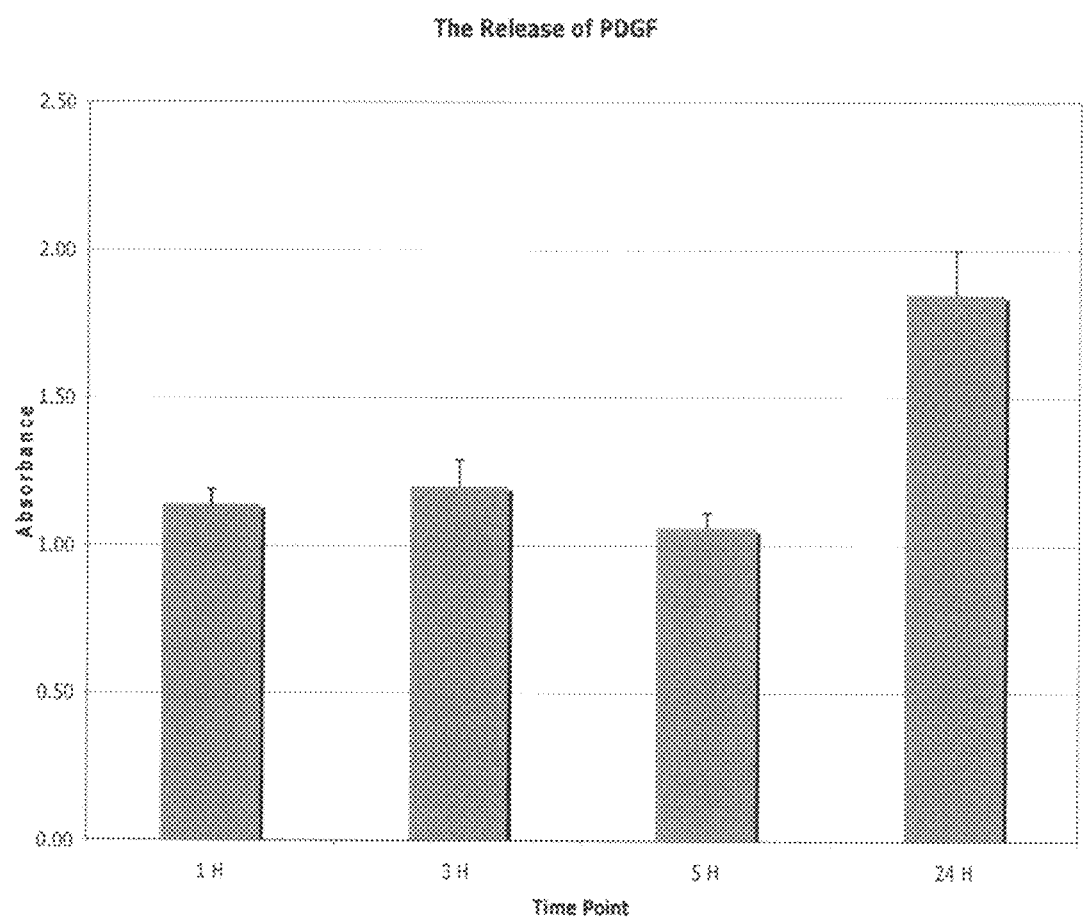
FIG. 5B shows the contrast of release rate of PDGF from titanium discs coated with HBP from Example 11 at various times, measured by absorbance, as described in Example 12.

Three titanium discs coated with the top-performing HBP composition from Example 11 (crosslinked thin coatings of TEGDA-phosphonate(25%)-polyurea) were incubated with 100 μL of PDGF (300 ng/mL in 0.2 M of NaAc) at 4° C. for three days. The discs were then washed three times with 200 μL of sterile water and placed in a 96 well plate, and 200 μL of NaAc solution was added into the wells containing the discs. The release of rhPDGF-BB was followed at RT, with solution removed for measurement in the plate reader after 1, 3, 5, 24 hrs, and fresh buffer was then added to the wells of the titer plate. The results are shown in FIG. 5B. Although the data for PDGF release is inconclusive at the 1, 3, and 5 hr measurement points, release after 24 hrs is well above the limit of detection, which demonstrates desirably long biological activities for PDGF adsorbed onto HBP coated titanium substrates.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A polymer delivery system comprising a polyurea hyperbranched polymer (HBP) having physiologically-acceptable anionic phosphorous groups for the in vivo binding and release of growth factors.

2. The polymer delivery system of claim 1 wherein the phosphorous groups are phosphonate anions or phosphate anions.

3. The polymer delivery system of claim 1 wherein the growth factors are orthobiologic growth factors (GF).

4. The polymer delivery system of claim 1 wherein the polymer is cross-linked using a cross-linking agent to form a network.

5. The polymer delivery system of claim 4 wherein the cross-linking agent is calcium or zinc ions, polyalanine or a dendrimer.

6. The polymer delivery system of claim 5 where a hydrogel is formed.

7. The polymer delivery system of claim 6 wherein thin hydrogel coatings of tetra(ethylene glycol)diacrylate (TEGDA)-phosphonate-polyurea HBP are crosslinked via coupling of acrylates of TEGDA.

8. The polymer delivery system of claim 1 wherein the polymer forms a coating on titanium, metal or plastic devices, which coating: a) retains and then releases the growth factors in vivo as biologically active agents; and b) retains the polymer.

9. The polymer delivery system of claim 8 wherein the coating is applied when the device is manufactured.

10. The polymer delivery system of claim 8 wherein the coating is applied to the device just prior to use or by injection at the site of use.

* * * * *